United States Patent [19]
Drubin et al.

[11] Patent Number: 5,972,640
[45] Date of Patent: Oct. 26, 1999

[54] METHODS FOR IDENTIFYING ANTIMITOTIC AGENTS

[75] Inventors: David G. Drubin; Georjana Barnes, both of Berkeley, Calif.

[73] Assignee: The Regents of the University of California, Oakland, Calif.

[21] Appl. No.: 09/076,587

[22] Filed: May 12, 1998

[51] Int. Cl.[6] .................................................. C12Q 1/18
[52] U.S. Cl. .................................. 435/32; 435/6; 435/29
[58] Field of Search .................................. 435/6, 29, 32, 435/172.3, 252.3, 320.1; 436/64

[56] References Cited

U.S. PATENT DOCUMENTS

| | | | |
|---|---|---|---|
| 5,604,113 | 2/1997 | White et al. | 435/29 |
| 5,674,996 | 10/1997 | Harwell et al. | 536/24.31 |
| 5,747,469 | 5/1998 | Roth et al. | 514/44 |

OTHER PUBLICATIONS

Tavormina P., Genetic Analysis of Mitotic Checkpoint Controls in the Yeast *Saccharomyces cerevisiae*, Dissertation Abstracts Int, 59(2B)513, Aug. 1998.

Chen Ray–Huei, Association of Spindle Assembly Checkpoint Component XMAD2 with Unattached Kinetochores, Science 274, Oct. 1996.

Hwang L., A Novel Yeast Screen for Mitotic Arrest Mutants Identifies DOC1, a New Gene Involved in Cyclin Proteolysis. Molecular Biology of the Cell vol. 8, 1877–1887, Oct. 1997.

*Primary Examiner*—Ralph Gitomer
*Attorney, Agent, or Firm*—Richard Aron Osman

[57] ABSTRACT

Antimitotic and antifungal agents are identified in screens comprising the steps of (a) contacting in culture first and second cells with an agent not previously known to be associated with mitotic arrest, wherein said cells differ in that the second cell has a functionally disrupted mitotic checkpoint; and (b) detecting a resultant sensitivity of the cells to the agent, whereby a higher sensitivity of the second cell identifies the agent as an antimitotic agent. The functionally disrupted mitotic checkpoint may be provided by a genetic mutation in a mad or bub gene, wherein mitotic arrest effects death of the cell. Yeast provide particularly useful cells for high throughput screens, including yeast transgenic in a human tubulin gene.

10 Claims, No Drawings

METHODS FOR IDENTIFYING ANTIMITOTIC AGENTS

FIELD OF THE INVENTION

The field of this invention is drug screens for antimitotic and antifungal agents.

BACKGROUND

We have developed a novel approach to identifying new antimitotic compounds to increase the arsenal of agents available for cancer and antifungal chemotherapy clinical trials. Antimitotic compounds are important reagents for basic research on mitosis, microtubule function, and cell cycle control. Previously identified antimitotic compounds bind to tubulin, the major mitotic spindle protein, and inhibit mitosis, thus blocking cell proliferation. Due to this latter activity, antimitotic compounds have proven successful for cancer chemotherapies in humans and agricultural antifungal chemotherapy. Antimitotics should also be effective antifungal agents in humans where fungal infections are a significant health problem. Because each antimitotic compound is effective for treating only a subset of cancers or fungi, and because each might have associated toxicities, it is important to identify new antimitotics.

Relevant Literature

Hoyt et al. (1991) Cell 66, 507–517 and Li et al. (1991) Cell 66, 519–531 describe genes required for cell cycle arrest in *S. cerevisiae*. Hartwell et al. (1997) U.S. Pat. No. 5,674,996 described cell cycle checkpoint genes. Hartwell et al. (1997) Science 278, 1064–1068, reviews genetic approaches to the discovery of anticancer drugs.

SUMMARY OF THE INVENTION

The invention provides methods and compositions for identifying antimitotic agents. The general methods comprise the steps of (a) contacting in culture first and second cells with an agent not previously known to be associated with mitotic arrest, wherein said cells differ in that the second cell has a functionally disrupted mitotic checkpoint; and (b) detecting a sensitivity or response of the cells to the agent, e.g. detecting a resultant mortality or morbidity of the cells, whereby a higher sensitivity of the second cell identifies the agent as an antimitotic agent. In a particular embodiment, the functionally disrupted mitotic checkpoint results from a genetic mutation in a mad or bub gene, wherein mitotic arrest effects death of the cell. Yeast provide particularly useful cells for high through-put screening, including yeast transgenic in a human tubulin gene. Generally, steps (a) and (b) are repeated in parallel or in series for a plurality of different agents not previously known to be associated with mitotic arrest. Accordingly, the invention provides a system for identifying an antimitotic agent comprising (a) a plurality of parallel culture pairs, each pair comprising first and second cells and a different agent not previously known to be associated with mitotic arrest, and (b) a positive control culture pair comprising first and second cells and an agent previously known to be associated with mitotic arrest, wherein said cells differ in that the second cell has a functionally disrupted mitotic checkpoint.

DETAILED DESCRIPTION OF PREFERRED EMBODIMENTS OF THE INVENTION

The following preferred embodiments and examples are offered by way of illustration and not by way of limitation.

Our procedures utilize cells characterized by a hypersensitivity to compounds that promote mitotic arrest. When normal cells are treated transiently with antimitotic compounds, they arrest the cell cycle at the mitotic (chromosome separation) phase until the compound is removed and microtubules re-assemble. The cells then enter into mitosis and complete a round of cell division. Mitotic arrest mutants do not arrest the cell cycle in response to antimitotic compounds. Since these mutants proceed in the cell division cycle in the absence of chromosome separation, they die. Our screen for antimitotic compounds involves transiently treating mitotic arrest mutants with libraries of defined compounds or natural products to identify agents that kill the mitotic arrest mutant yeast cells, but not wild-type yeast. The subject screens, and particularly the budding yeast-based screen, provide numerous advantages over current screening methods. The subject methods are simple, sensitive and specific, facilitating large scale screening, automation, and purification of compounds. The methods are biological assays such that the identified compounds necessarily cross the plasma membrane to be exposed to cell's metabolic machinery. In particular embodiments, the methods are microbiological, permitting replica-plating, sampling large numbers of cells, etc., and exploit yeast, the most genetically tractable eukaryote having well-characterized biology. For example, revertants identify targets of agents and possible modes of developing resistance; information about frequency important for anti-fungal applications. Furthermore, morphology, cdc mutants, etc., identify targeted process. The methods also encompass non-tubulin mitotic targets. In addition, host specificity may be effected; for example, benomyl, important agricultural antifungal agent, is active against yeast but not mammalian microtubules. Finally, known antimitotics may be advantageously combined with other pharmacologically active agents, including anticancer and antifungal agents.

The first step of the general methods involves contacting in culture first and second eukaryotic cells with an agent not previously known to be associated with mitotic arrest, wherein said cells differ in that the second cell has a functionally disrupted mitotic checkpoint. In a preferred embodiment, the cells are identical but for the disruption of the mitotic checkpoint. A wide variety of suitable eukaryotic cells are either commercially available or readily derived. For example, in one embodiment, the cells are transformed mammalian cells, such as human CIN cell lines available from the Johns Hopkins Oncology Center (Baltimore, Md.) by email request to lengauer@welchlink.welch.jhu.edu. Alternatively, suitable mammalian cells may be produced by transfecting cells with checkpoint mutant allele expression vectors, e.g. as described by Cahill, et al. (1998) Nature 392, 300–303. For example, a pBIBub1 expression vector may be constructed by cloning RT-PCR products representing the hBUB1 (accession number AF046078), the Bub 1V400 and the Bub1V429 sequences into the NotI and SalI stipes of pBI (Clontech). HCT116 or DLD1 cells may be then contransfected with the vector DNA and DNA from a plasmid driving the expression of the tTA transcriptional activator (Clontech) and Lipofectamine (Life Technologies). In another embodiment, the cells are fungal cells, including pathogenic fungi such as *Candida albicans*, *Aspergillus flavus/fumigatus*, etc. (see, e.g. McGinnis and Tyring (1997) in Medical Microbiology, Ed. S. Baron, p.897–899). As indicated above, yeast provide particularly convenient cells, especially industrially applied species such as *P. pastoris* and *S. cerevisiae*. The cells may be modified in a wide variety of ways to more accurately model the targeted cell type. For example, S. cerevisiae may be genetically modified to express heterologous genes, including pathogenic fungi specific genes, human specific genes such as tubulin genes, etc.

The second cell has a functionally disrupted mitotic checkpoint wherein agents which would otherwise effect mitotic arrest instead effect a sensitivity or response of the cell, preferably manifested as a readily detectable phenotypic change in the cell, such as a change in cell morphology, metabolic activity, e.g. change in the expression or activity of a marker enzyme, growth rate, viability, etc. The disruption may be effected by a variety of means, including chemical/pharmacological disruption, e.g. with checkpoint inhibitory drugs, or by genetic disruption, e.g. genetic mutation in a spindle checkpoint component or target, such as a mad or bub gene (supra), an MPS gene (e.g. Schutz et al., 1998, Mol Biol Cell 9, 759–774; Winey, et al., 1991, J Cell Biol. 114, 745–754), a Cdc20 gene (e.g. Hwang L H, et al., 1998, Science 279, 1041–1044; Tavormina P A, et al., 1998, Genetics 148, 1701–1713), etc. For example, suitable genetic mutants may be generated in mammalian cells according to the method of Cahill, et al. (1998) Nature 392, 300–303 or in yeast as described in Hoyt et al. (1991) Cell 66, 507–517 and Li et al. (1991) Cell 66, 519–531.

Candidate agents not previously known to be associated with mitotic arrest encompass numerous chemical classes, though typically they are organic compounds; preferably small organic compounds and are obtained from a wide variety of sources including libraries of synthetic or natural compounds. The agents are provided at a concentration to avoid significant acute toxicity to the targeted cells, generally by assaying serial dilutions. Preferred agents act specifically on mitotic function and not by damaging DNA either directly or indirectly. Accordingly, in a particular embodiment, the methods also involve determining whether the agent effects DNA damage, e.g. using DNA damage checkpoint mutants such as RAD9 or measuring induction of DNA damage specific transcriptional activation as described by Barnes and Rio (1997) Proc Natl Acad Sci USA, 94(3):867–872.

The second step of the general methods involves detecting a sensitivity or response of the cells to the agent, whereby a higher sensitivity of the second cell identifies the agent as an antimitotic agent. Detection may be accomplished by any convenient means, depending on the cell type and the nature of the disrupted mitotic checkpoint. For many applications, the mitotically arrested cells exhibit a readily identifiable phenotype which may be distinguished directly, e.g. visually, mechanically (e.g. by cell adhesion), etc., or indirectly, e.g. by the binding of a marker specific antibody, the metabolism of a marker-substrate, etc. The higher sensitivity may be measured in terms of a single cell (e.g. probability of cell death) or in terms of a population of cells (e.g frequency of cell death) and a higher sensitivity is reflected in a statistically significant difference.

For high throughput applications, the contacting and detecting steps are repeated in parallel or in series for a plurality of different agents not previously known to be associated with mitotic arrest. Accordingly, the invention provides a system for identifying an antimitotic agent comprising a plurality of parallel test culture pairs, each pair comprising first and second cells and a different agent not previously known to be associated with mitotic arrest, a positive control culture pair comprising first and second cells and an agent previously known to be associated with mitotic arrest, and a negative control culture pair comprising first and second cells and an agent (e.g. solvent blank) previously known not to be associated with mitotic arrest, wherein the first and second cells of each pair of each group differ in that the second cell has a functionally disrupted mitotic checkpoint.

EXAMPLES

1. Assay Procedures

Initially, we established conditions to identify compounds that inhibit yeast growth by blocking mitosis, in mutant yeast having mutations which result in a defect in mitotic arrest in response to antimitotic compounds. Brief exposure to antimitotic compounds, or chronic exposure to normally sublethal levels of compound, cause these mutants to die. We first tested agents known to block yeast cells in mitosis (e.g. nocodazole and benomyl). As controls for the specificity of the screen, we used agents that block yeast cells in other phases of the cell cycle (e.g., hydroxylurea, an S phase blocker). After establishing and optimizing screening conditions, initially assayed compounds are the large collection of compounds shown to block mammalian cells in mitosis, but not previously tested for yeast (see Mareel, M. M. and De Mets, M. (1984) Int Rev Cytol 90:125–168, for a review of compounds).

Screening procedures were systematically varied on each of the six mutants defective in mitotic arrest to identify the optimal procedure and mutant strain. In initial screens, lawns of wild type and mitotic arrest mutant cells are plated on plates containing rich growth medium, and filter discs soaked in the test compound are placed on these plates, as per routine yeast filter disc growth inhibition assays. A range of concentrations are tested for each compound. For compounds which specifically effect mitosis, the mitotic arrest mutant is more sensitive to the compound, providing a larger ring of growth inhibition around the filters placed on the mutant lawn when compared to the wild type lawn.

In a second procedure, cells are treated transiently with antimitotic agents at high levels, and then viability is scored. Using a multipronged inoculator device we plate dilution series of wild type and mitotic arrest defective mutant cells in 96-well plates containing antimitotic compounds. After variable incubation times we use velvet replica-platers to transfer the cells to rich plates on which the cells are grown over night. Cell growth is detected for all dilutions of wild type cells, but growth is detected for only the most concentrated mutant cells. Optimal screening conditions are optimized by systematically altering variables as described above.

Antimitotic specificity of compounds is confirmed by (1) examining the morphology of wild type yeast arrested with the compound (yeast arrested at mitosis have a large budded morphology, Huffaker, et al. (1988) J. Cell Biol. 106, 1997–2010; Jacobs, et al. (1988) J. Cell Biol. 107, 1409–1426); (2) performing anti-tubulin immunofluorescence to identify spindle defects caused by the compound; and (3) testing whether hydroxylurea, an S phase cell cycle blocker, prevents cell death caused by transient treatment with the test compound (Li, R. and Murray, A. W. (1991) Cell 66, 519–531). In addition to being potential agents for cancer chemotherapy, the newly discovered agents are useful in investigating microtubule function.

In a particular embodiment, we use yeast transgenic in human tubulin genes. Plasmids bearing the human α- and β-tubulin genes expressed under the control of the yeast α- and β-tubulin promoters are introduced into yeast cells (Wertman, K. F., Drubin, D. G. and Botstein, D. (1992) Genetics 132, 337–350) that have chromosomal copies of the yeast tubulin genes disrupted, but are viable because they carry the yeast tubulins on a plasmid. By selecting against a marker gene carried on the plasmid that bears the yeast tubulins, the cells are forced to lose the yeast tubulin genes. To minimize negative impacts of the heterologous human tubulins function, plasmids may be selected for targeted copy number. Validation is effected by demonstrating sensitivity of the transgenic yeast to colchicine and taxol, antimitotic compounds that inhibit mammalian, but not yeast, microtubule assembly.

2. Yeast Assay Protocol

1. A wildtype A346a yeast strain and a congenic mad1-1 mutant strain are grown to early log phase (~$10^6$ cells/ml).

2. The exact cell density of each culture is determined by counting on a hemocytometer.

3. The cultures are then diluted to ~10 cells/microliter, and 45 microliters of the diluted cells is added to each well of a 96-well microtiter dish using a multi-pipeter device.

4. 5 microliters of each of the fungal extracts (natural products), stored in 50% DMSO in 96-well microtiter dishes, is pipetted into the corresponding well of the cell-containing microtiter dish, using a multi-pipeter device. A control that contains only 50% DMSO is also included.

5. The microtiter dishes containing cells and fungal extracts are covered and incubated at room temperature for 4 hours on a nutator mixer.

6. 5 microliters of cells from each well is then spotted onto a YPD plate. Each 96 well microtiter dish requires two YPD plates.

7. The plates are incubated at 30 degrees centigrade for 3 days before scoring for the number of colonies in each spot.

8. Extracts that reduce the colony number of the mutant strain to a greater extent than they do that of the wildtype strain are re-examined.

3. Exemplary Yeast Assay Results: summarized results from an exemplary screen of ~2700 extracts in twenty eight 96 well microtiter plates.

|   | First Pass | After re-Testing |
|---|---|---|
| a. Effects wild-type > mad1 | 20 | 0 |
| b. Effects mad1 > wild-type | 50 | 7 |
| c. Effects mad1 = wild-type | 47 | 12 |

4. Mammalian Clonogenic Cytotoxicity Assay Protocol

In this method, sub-confluent dishes of mammalian cells in culture are treated for predetermined times and/or dosages of compounds, the cells are resuspended, diluted, and plated at low density on a new plate to form clonal colonies. Cell mortality is scored by visual/optical detection of a decrease in the number of emergent or surviving clones.

1. Parallel cultures of transformed (human fibroblasts transfected with a pBIBub 1 expression vector constructed by cloning hBUB1 (accession number AF046078), the Bub1V400 and the Bub1V429 sequences into the NotI and SalI stipes of pBI (Cahill, et al. (1998) Nature 392, 300–303; Clontech)) and wild-type human fibroblasts are grown to confluence in 100 mm culture plates (approx. $5 \times 10^6$ cells).

2. 5 microliters of each of the fungal extracts, stored in 50% DMSO in 96-well microtiter dishes, is pipetted into corresponding cell cultures, using a multi-pipeter device. Positive (effective concentration of known antimitotic) and negative (50% DMSO only) control cultures are also provided.

3. The cultures are covered and incubated at 37° C. for 12 hours on rocker.

4. The cells of each culture are resuspended, diluted in fresh culture medium to a density of about $1 \times 10^4$ cells/100 mm culture plate.

5. The plates are incubated at 37° C. for 3 days before scoring for the number of cell colonies surviving in each culture with a fluorescent vital dye (Molecular Probes) to detect viability.

6. Extracts that reduce the colony number of the transformed cell cultures to a greater extent than they do that of the wildtype cultures are re-examined.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying an antimitotic agent comprising the steps of:

(a) contacting in culture first cells and second cells with an agent not previously known to be associated with mitotic arrest, wherein said first cells and said second cells differ in that the second cells have a functionally disrupted mitotic checkpoint, whereby the agent causes a greater detectable phenotypic change in the second cells than the first cells; and (b) detecting a phenotypic change in the first cells and said second cells in response to the agent, whereby a greater phenotypic change in the second cells than in the first cells identifies the agent as an antimitotic agent.

2. The method of claim 1 wherein the phenotypic change is detected as mortality of the first cells and second cells.

3. The method of claim 1 wherein the second cells have a functionally disrupted mitotic checkpoint resulting from a genetic mutation.

4. The method of claim 1 wherein the second cells have a functionally disrupted mitotic checkpoint resulting from a genetic mutation in at least one of a Mad, Bub, MPS1 or Cdc20 gene.

5. The method of claim 1 wherein the first cells and second cells are yeast.

6. The method of claim 1 wherein the first cells and second cells are yeast comprising a human tubulin gene.

7. The method of claim 1 wherein steps (a) and (b) are repeated in parallel or in series for a plurality of different agents not previously known to be associated with mitotic arrest.

8. The method of claim 1 wherein the phenotypic change is detected as mortality of the first cells and second cells, the first cells and second cells are yeast and steps (a) and (b) are repeated in parallel or in series for a plurality of different agents not previously known to be associated with mitotic arrest.

9. The method of claim 8 wherein the second cells have a functionally disrupted mitotic checkpoint resulting from a genetic mutation.

10. The method of claim 8 wherein the second cells have a functionally disrupted mitotic checkpoint resulting from a genetic mutation in at least one of a Mad, Bub, MPS1 or Cdc20 gene.

* * * * *